United States Patent
Lee et al.

(10) Patent No.: US 7,063,968 B2
(45) Date of Patent: Jun. 20, 2006

(54) ORGANIC ACID PRODUCING MICROORGANISM AND PROCESS FOR PREPARING ORGANIC ACIDS EMPLOYING THE SAME

(75) Inventors: Sang Yup Lee, Daejeon (KR); Ho Nam Chang, Daejeon (KR); Pyung Cheon Lee, Daejeon (KR); Woo-gi Lee, Daejeon (KR)

(73) Assignees: Bisinformatix, Inc. (KR); Korea Advanced Institute of Science and Technology (KR)

( * ) Notice: Subject to any disclaimer, the term of this patent is extended or adjusted under 35 U.S.C. 154(b) by 542 days.

(21) Appl. No.: 10/312,932

(22) PCT Filed: Jun. 29, 2001

(86) PCT No.: PCT/KR01/01127

§ 371 (c)(1),
(2), (4) Date: Dec. 30, 2002

(87) PCT Pub. No.: WO02/00846

PCT Pub. Date: Jan. 3, 2002

(65) Prior Publication Data

US 2003/0113885 A1 Jun. 19, 2003

(30) Foreign Application Priority Data

Jun. 29, 2000 (KR) .............................. 2000-36645

(51) Int. Cl.
*C12P 7/40* (2006.01)
*C12P 7/54* (2006.01)
*C12P 7/56* (2006.01)
*C12N 1/20* (2006.01)

(52) U.S. Cl. ................... 435/136; 435/139; 435/140; 435/145; 435/252.1

(58) Field of Classification Search ............... 435/136, 435/139, 140, 145, 252.1
See application file for complete search history.

(56) References Cited

OTHER PUBLICATIONS

"Succinic acid production by *Anaerabiospirillum succiniciproducens*: effects of the H2/CO2 supply and glucose concentration"; Authors: Pyung Cheon Lee, Woo Gi Lee, Sunhoon Kwon, Sang Yup Lee and Ho Nam Chang; Elsevier Science Inc.; Enzyme and Microbial Technology, vol. 24; 1999; pp. 549-554.

"*Anaerobiospirillum*, a New Genus of Spiral-Shaped Bacteria"; Authors: C. P. Davis, d. Cleven, J. Brown and E. Balish; International Journal of Systematic Bacteriology; International Association of Microbiological Societies, vol. 26, No. 4; Oct. 1976; pp. 498-504.

"Chemical and Fuel Production by Anaerobic Bacteria"; Author: J. G. Zeikus; Ann. Rev. Microbiol., vol. 34; 1980; pp. 423-464.

International Search Report; International application No. PCT/KR01/01127; International filing date: Jun. 29, 2001; Date of Mailing: Oct. 31, 2001.

International Preliminary Examination Report; International application No. PCT/KR01/01127; International filing date: Jun. 29, 2001; Date of Completion: Oct. 11, 2002.

*Primary Examiner*—Herbert J. Lilling
(74) *Attorney, Agent, or Firm*—Canton Colburn LLP (57) ABSTRACT

A novel microorganism capable of producing organic acids, *Mannheimia* sp. 55E, and a process for producing organic acid through anaerobic and aerobic incubation using the novel microorganism are provided. The method of producing an organic acid using the microorganism involves incubating *Mannheimia* sp. 55E with Accession Number KCTC 0769BP in a medium under anaerobic or aerobic conditions and obtaining an organic acid from the medium. *Mannheimia* sp. 55E produces succinic acid, lactic acid, and formic acid under anaerobic conditions saturated with $CO_2$, and succinic acid, lactic acid, acetic acid, and formic acid under aerobic or $N_2$ anaerobic conditions. *Mannheimia* sp. 55E is a facultative anaerobe tolerant of oxygen. Thus, the use of *Mannheimia* sp. 55E in producing organic acids can eliminate a problem of process instability, which would occur by the presence of oxygen in a fermentation process of producing organic acids using an obligate anaerobic microorganism.

10 Claims, 5 Drawing Sheets

FIG. 5

ORGANIC ACID PRODUCING MICROORGANISM AND PROCESS FOR PREPARING ORGANIC ACIDS EMPLOYING THE SAME

BACKGROUND OF THE INVENTION

1. Field of the Invention

The present invention relates to a microorganism capable of producing organic acids and a process for producing organic acids using the microorganism, and more particularly, to a new microorganism, *Mannheimia* sp. 55E, capable of producing organic acids and a process for producing organic acids through incubation of the microorganism in anaerobic or aerobic conditions.

2. Description of the Related Art

Thanks to the progress of the petrochemical industry, most chemical substances have been produced from petroleum and natural gases. However, restrictions on the production of chemical substances is becoming more rigid worldwide with the recent rise of environmental concerns such as global warming, thereby increasing the need for the development of an alternate to the conventional process of producing chemicals.

The rapid advance of microorganism cultivation and genetic engineering technology has placed biochemical productions of chemical substances at a competitive position to the conventional petrochemical process. Biochemical methods are known to be environmentally compatible, thus being capable of solving environmental problems, because they can suppress generation of gases that cause global warming, such as carbon dioxide ($CO_2$), with use of inexpensive renewable resources. Therefore, approaches to cost reduction through isolation of new strains and process improvement are getting spread in the biochemical field. In addition, increased market values of biochemical materials have boosted research into the production of the biochemical materials from biomass using microorganisms throughout the world.

In particular, focus on biochemical materials, particularly succinic acid and lactic acid, is increasing due to their cost competitiveness and wide applications as biodegradable plastic monomers, food additives, and intermediate products of other organic compounds.

A study on the biological production of succinic acid was started in 1938 by Lockwood who reported production of succinic acid from sugar using *Fusarium martii* with a 18% yield. It was reported that production of succinic acid through glycolysis of a variety of anaerobic microorganisms such as *Succinivibrio dextrinosolvens, Fibrobacter succinogenes*, and *Ruminococcus flavefaciens* (Zeikus, Annu, Rev. Microbiol., 34:423–464, 1980). Any microorganism capable of producing succinic acid with high yield for industrial use, except for *Anaerobiospirillum succiniciproducens* known to be able to produce succinic acid from glucose with high yield and concentration in the presence of excess carbon, was not disclosed (David et al., *Int. J. Syst. Bacteriol.*, 26:498–504, 1976). Because *Anerobiospirillum succiniciproducens* is an obligate anaerobic microorganism, stable fermentation using the microorganism for production of the succinic acid is not ensured even with the presence of trace oxygen.

A variety of factors, such as production yield, fermentation conditions, etc., should be carefully considered for economical production of organic acids through microorganism fermentation. In particular, isolation of new microorganisms capable of producing organic acids has priority over the other factors to consider. Most microorganisms currently available to produce organic acids are anaerobic microorganisms, so costly cultivation equipment is required, and it is very likely that intended fermentation fails due to the presence of trace oxygen. Therefore, there is an urgent need for development of microorganisms having a tolerance to oxygen and capable of producing organic acids with high yield.

As a result of research on such oxygen-tolerant microorganisms being able to produce organic acids with high throughput, the present inventors have succeeded in separating a new facultative anaerobe, *Mannheimia* sp. 55E, from the bovine rumen fluid, and identifying the new microorganism to be tolerant of oxygen and able to produce organic acids in anaerobic and aerobic conditions.

SUMMARY OF THE INVENTION

It is a first object of the present invention to provide a new microorganism, *Mannheimia* sp. 55E (KCTC 0769BP), capable of producing organic acids.

It is a second object of the present invention to provide a process for producing organic acids under anaerobic and aerobic conditions using the microorganism.

To isolate a new microorganism tolerant of oxygen and capable of producing organic acids with high yield, the present inventors inoculated dilute samples from the rumen fluid on a solid medium to give rise to individual colonies and incubated on a growth medium containing excess carbon dioxide ($CO_2$) to screen strains having the ability to produce succinic acid. The screened strain was subjected to 6S rDNA analysis to determine whether they have similarity to previously known strains. As a result, the isolated strain was identified as a new microorganism with a 95% similarity to *Mannheimia varigena* and designated as *Mannheimia* sp. 55E. A deposit of *Mannheimia* sp. 55E was made Apr. 10, 2000 to the Korean Collection for Type Cultures (KCTC), an International Depository Authority (IDA) in Korea Research Institute of Bioscience and Biotechnology (KRIBB) (52 Oun-dong, Yusong-gu, Taejon, Republic of Korea) and was given Accession Number KCTC 0769BP.

*Mannheimia* sp. 55E identified in the present invention is facultative anaerobic, gram-negative, non-motile, appears as rods or *coccobacilli,* does not form endospores, and has the ability to produce organic acids such as succinic acid, lactic acid, acetic acid, formic acid, etc. *Mannheimia* sp. 55E has a growth temperature range of 30–50° C. with an optimal growth temperature of 39° C. and a pH range of 6.0–7.5 with an optimal pH of 6.5.

A process for producing organic acids using *Mannheimia* sp. 55E involves incubating *Mannheimia* sp. 55E (KCTC 0769BP) under anaerobic or aerobic conditions and obtaining organic acids therefrom. The anaerobic conditions are created with a supply of carbon dioxide ($CO_2$) or nitrogen at a flow rate of 0.1–0.4 vvm, preferably 0.2–0.3 vvm, and most preferably 2.25 vvm. The aerobic conditions are created with a supply of oxygen ($O_2$) at a flow rate of 0.5–1.0 vvm, preferably 0.7–0.8 vvm, and most preferably 0.75 vvm.

Any medium is available for the culture of *Mannheimia* sp. 55E without limitations, but preferably the content of glucose in a medium is in the range of 5–60 g/L, and most preferably 20 g/L. The incubation is carried out at a temperature of 35–45° C., preferably at a temperature of 38–41° C., and most preferably at 39° C., and at pH 6.0–7.5, preferably at pH 6.3–6.7, and most preferably at pH 6.5.

Lactic acid, citric acid, succinic acid, or formic acid is produced under the anaerobic conditions. It is preferable to produce the anaerobic conditions using $CO_2$ for higher yield of succinic acid and $N_2$ for higher yield of lactic acid. Lactic acid, citric acid, or formic acid is produced under the aerobic conditions with the lactic acid having the highest yield.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will be described in greater detail by means of the following examples. The following examples are for illustrative purposes and are not intended to limit the scope of the invention.

EXAMPLE 1

Isolation and Identification of *Mannheimia* sp. 55E by 16S rDNA Sequence Analysis 1 ml of the bovine rumen fluid was subjected to 100 fold dilution with a medium consisting of 20 g of glucose, 5 g of polypeptone, 5 g of yeast extract, 3 g of $K_2HPO_4$, 1 g of NaCl, 5 g of $(NH_4)_2SO_4$, 0.2 g of $CaCl_2.2H_2O$, 0.2 g of $MaCl_2.6H_2O$, and 5 g of $Na_2CO_3$ per liter, followed by plating on a 1%-agarose solid medium having the same composition as the medium above and incubation for 10 hours. Individual colonies were isolated from the cultures and transferred to and incubated in 3 ml of the above medium saturated with $CO_2$ for 10 hours. The yield of succinic acid in the medium was measured by high performance liquid chromatography (HPLC, Aminex HPX-87H column, Bio-Rad, U.S.A.), and a strain producing succinic acid with a 50% or greater yield was screened. As a result of a physiological property assessment on the screened strain, the screened strain was found to be gram negative and non-endospore forming. The strain growth was observed at a temperature of 30–50° C. with the optimal growth temperature of 39° C., and at a pH of 6.0–7.5 with the optimal growth pH of 6.5.

Genomic DNA was isolated from the screened strain by applying the Rochelle's method (Rochelle et al., FEMS Microbiol., Lett., 100:59–66, 1992). Polymerase chain reaction (PCR) was carried out using the isolated genomic DNA as a template, primer 1 (5'-AGAGTTTGATCMTGGCTCAG-3' (SEQ ID NO. 1)), and primer 2 (5'-AAGGAGGTGWTCCARCC-3' (SEQ ID NO. 2)) to amplify 16S rDNA. The sequence of the amplified products of 16S rDNA was identified, and the similarity of the 16S rDNA to other known strains was analyzed using a DNA sequence analysis program, PHYLIP (PHYlogeny Inference Package, version 3.5c). Table 1 shows the result of the similarity analysis for species, and FIG. 1 is a phylogenetic tree constructed through the similarity analysis.

Figure 1:
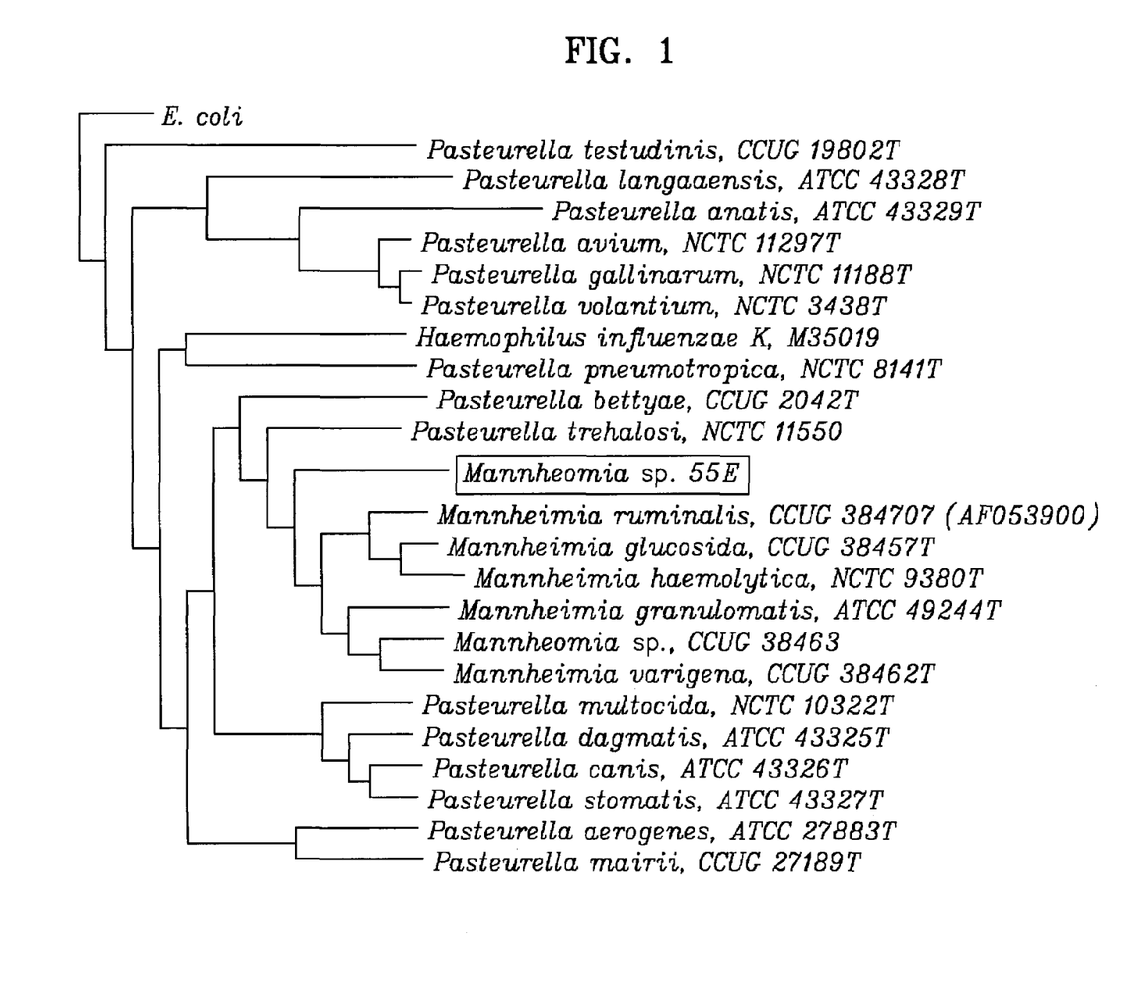
FIG. 1 is a phylogenetic tree constructed by 16S RNA analysis for *Mannheimia* sp. 55E.

As shown in Table 1 and FIG. 1, the isolated strain is proved to be a new strain that belongs to the *Mannheimia* genus in the *Pasteurellaceae* family with a 95.1% similarity to *Mannheimia variaena*, and designated *Mannheimia* sp. 55E. A deposit of *Mannheimia* sp. 55E was made Apr. 10, 2000 to the Korean Collection for Type Cultures (KCTC), an International Depository Authority (IDA) in Korea Research Institute of Bioscience and Biotechnology (KRIBB) (52 Oun-dong, Yusong-gu, Taejon, Republic of Korea) and was given Accession Number KCTC 0769BP.

TABLE 1

Results of 16S r DNA Analysis for Similarity

| Species | Code No. | Similarity |
|---|---|---|
| *Mannheimia varigena* (CCUG 38462T) | AF053893 | 95.1 |
| *Mannheimia granulomatis* (ATCC 49244T) | AF053902 | 94.9 |
| *Mannheimia ruminalis* (CCUG 38470T) | AF053900 | 94.7 |
| *Mannheimia glucosida* (CCUG 38457T) | AF053889 | 94.7 |
| *Pasteurella trehalosi* (NCTC 11550) | U57073 | 94.7 |
| *Pasteurella dagmatis* (ATCC 43325T) | M75051 | 94.3 |
| *Mannheimia haemolytica* (NCTC 9380T) | AF060699 | 94.1 |
| *Pasteurella avium* (NCTC 11297T) | M75058 | 94.0 |
| *Pasteurella aerogenes* (ATCC 27883T) | M75048 | 94.0 |
| *Pasteurella bettyae* (CCUG 2042T) | L06088 | 94.0 |
| *Pasteurella volantium* (NCTC 3438T) | M75070 | 93.8 |

TABLE 1-continued

Results of 16S r DNA Analysis for Similarity

| Species | Code No. | Similarity |
| --- | --- | --- |
| Pasteurella mairii (CCUG 27189T) | AF024532 | 93.8 |
| Pasteurella multocida (NCTC 10322T) | M35018 | 93.8 |
| Pasteurella langaaensis (ATCC 43328T) | M75053 | 93.7 |
| Pasteurella gallinarum (NCTC 11188T) | M75059 | 93.5 |
| Pasteurella stomatis (ATCC 43327T) | M75050 | 93.2 |
| Pasteurella canis (ATCC 43326T) | M75049 | 93.1 |
| Haemophilus influenzae T | M35019 | 92.5 |
| Pasteurella pneumotropica (NCTC 8141T) | M75083 | 92.3 |
| Pasteurella anatis (ATCC 43329T) | M75054 | 92.0 |
| Pasteurella testudinis (CCUG 19802T) | L06090 | 91.3 |
| Vibrio cholerae (ATCC 14035T) | Z21856 | 87.8 |
| E. coli | J01695 | 86.6 |

EXAMPLE 2

Characteristics of *Mannheimia* sp. 55E

Figure 2:
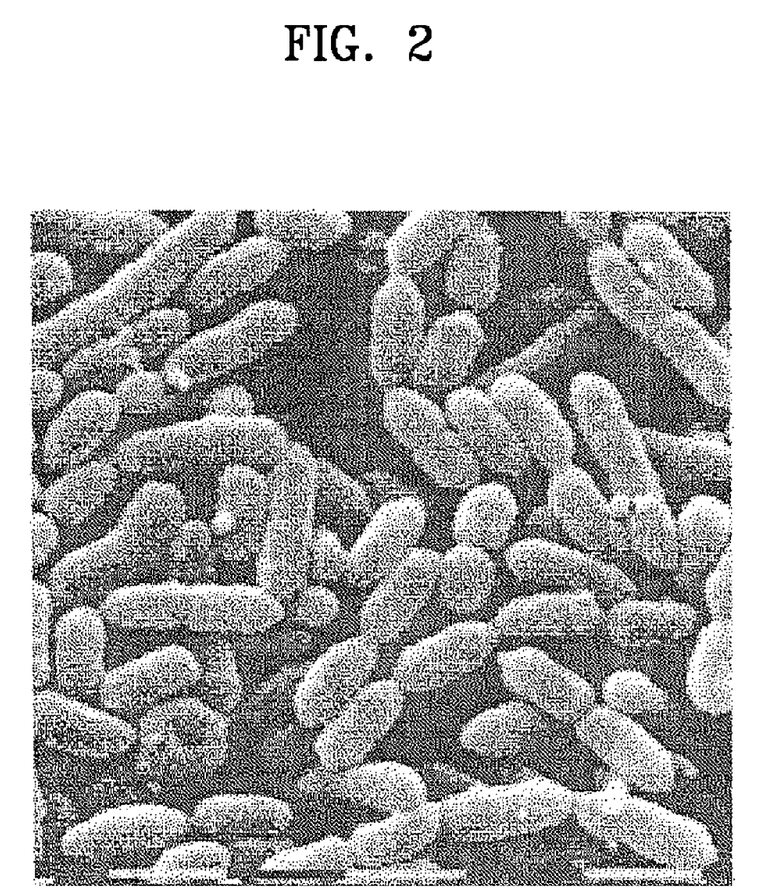
FIG. 2 is a scanning electron microscope (SEM) photo showing the morphological characteristics of *Mannheimia* sp. 55E.

*Mannheimia* sp. 55E was cultured on a blood agar plate, which is known to be suitable for the growth of *Mannheimia* species, at 39° C. for 24 hours. As a result, colonies having a diameter of 1–2 mm with smooth greyish surface were observed. Single cells of *Mannheimia* sp. 55E were observed using a scanning electron microscope (SEM). As shown in FIG. 2, cells of *Mannheimia* sp. 55E appear as rods or *coccobaccilli* having dimensions 0.3–0.5 by 1.0 microns.

EXAMPLE 3

Fermentation Characteristics of *Mannheimia* sp. 55E Under Anaerobic Conditions Saturated with $CO_2$ To investigate fermentation power of *Mannheimia* sp. 55E, it was incubated under anaerobic conditions saturated with $CO_2$, and the reaction products were analyzed.

100 ml of a pre-culture medium consisting of 20 g of glucose, 5 g of polypeptone, 5 g of yeast extract, 3 g of $K_2HPO_4$, 1 g of NaCl, 1 g of $(NH_4)_2SO_4$, 0.2 g of $CaCl_2.2H_2O$, 0.2 g of $MaCl_2.6H_2O$, and 10 g of $MgCO_3$ per liter was prepared, and $CO_2$ gas was supplied to the medium. Inoculation of *Mannheimia* sp. 55E was followed by pre-culture at 39° C. for 9 hours.

0.9 ml of a main culture medium consisting of 20 g of glucose, 5 g of polypeptone, 5 g of yeast extract, 3 g of $K_2HPO_4$, 1 g of NaCl, 1 g of $(NH_4)_2SO_4$, 0.2 g of $CaCl_2.2H_2O$, 0.2 g of $MaCl_2.6H_2O$, and 10 g of $MgCO_3$ per liter was placed inside a 2.5 L incubator. 100 ml of the pre-culture of succinic acid producing microorganism was transferred to the main culture medium, followed by fed-batch culture at 39° C. at pH 6.5 with supply of $CO_2$ gas at a flow rate of 0.25 vvm. Culture media were sampled at 1-hour intervals during the incubation and cell concentration, and the amounts of succinic acid, glucose, acetic acid, and formic acid were measured by a spectrophotometer (Ultraspec 3000, Pharmacia Biotech., Sweden).

Figure 3:
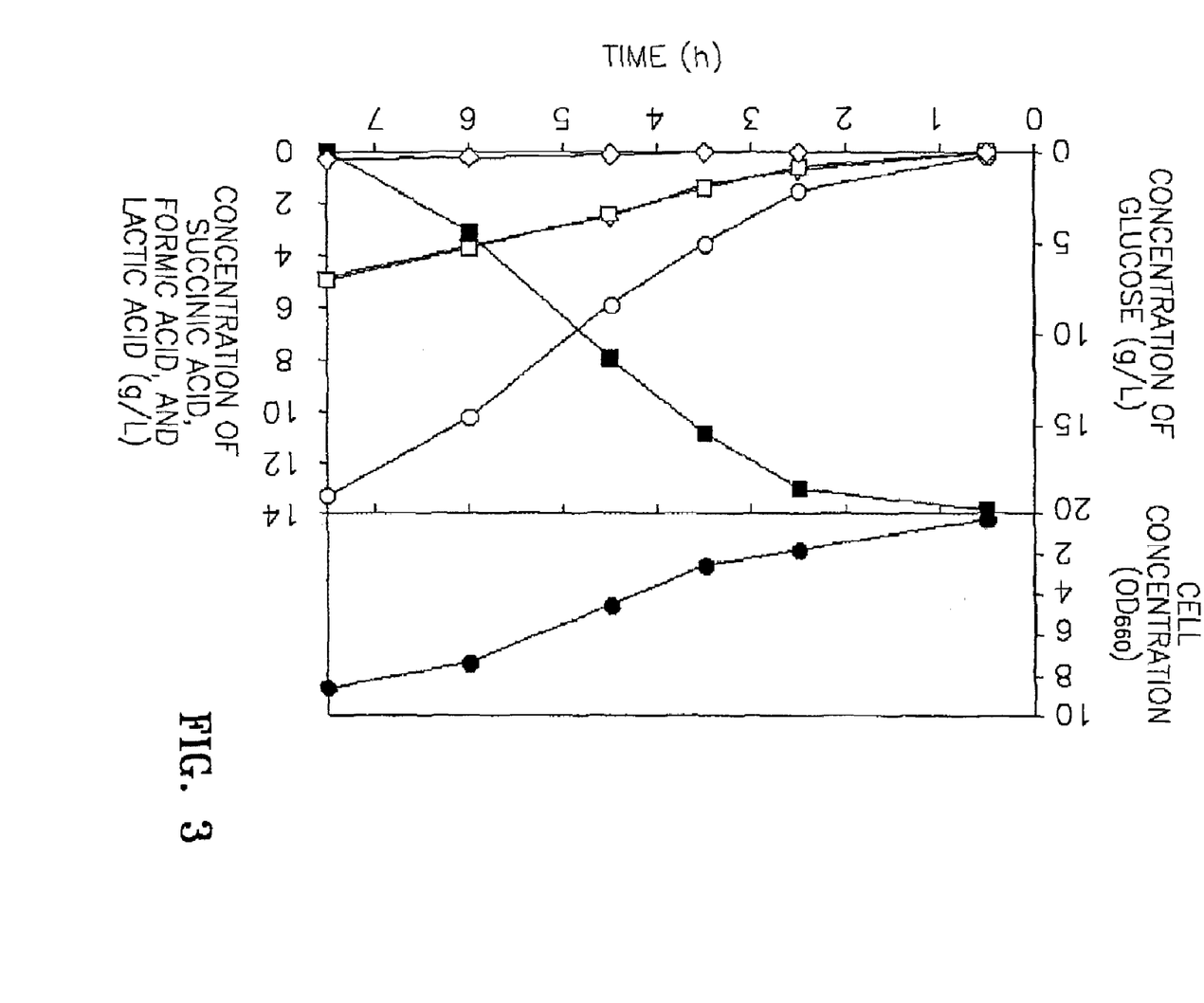
FIG. 3 is a graph showing the fermentation characteristics of *Mannheimia* sp. 55E under anaerobic conditions saturated with $CO_2$.

FIG. 3 is a graph showing variations in concentration of cells (●), succinic acid (○), glucose (■), lactic acid (◇), and formic acid (□) with respect to incubation time. As shown in FIG. 3, after a 7.5-hour incubation, 19.8 g/L of glucose is consumed, and 13.3 g/L lactic acid is produced with a yield of 67% (amount of produced succinic acid per amount of consumed glucose). Volumetric productivity for succinic acid (amount of produced succinic acid per hour) is 1.8 g/L/h.

The method of producing succinic acid using *Mannheimia* sp. 55E under anaerobic conditions saturated with $CO_2$ has a slightly lower yield, but about 80% greater volumetric productivity than a conventional anaerobic method of producing succinic acid using *Anaerobiospirillum succiniciproducens* (ATCC 29305) (Lee et al., *Enzyme Microbiol. Technol.*, 24:549–554, 1999).

EXAMPLE 4

Fermentation Characteristics of *Mannheimia* sp. 55E Under Anaerobic Conditions Saturated with $N_2$ To investigate fermentation power of *Mannheimia* sp. 55E under anaerobic conditions saturated with $N_2$, incubation was carried out for 22 hours in the same manner as in Example 3, except that nitrogen was supplied at a flow rate of 0.25 vvm. Culture media were sampled at 1-hour intervals during the incubation, and cell concentration and the amounts of lactic acid, glucose, formic acid, acetic acid, and succinic acid were measured by the same method as in Example 3.

Figure 4:
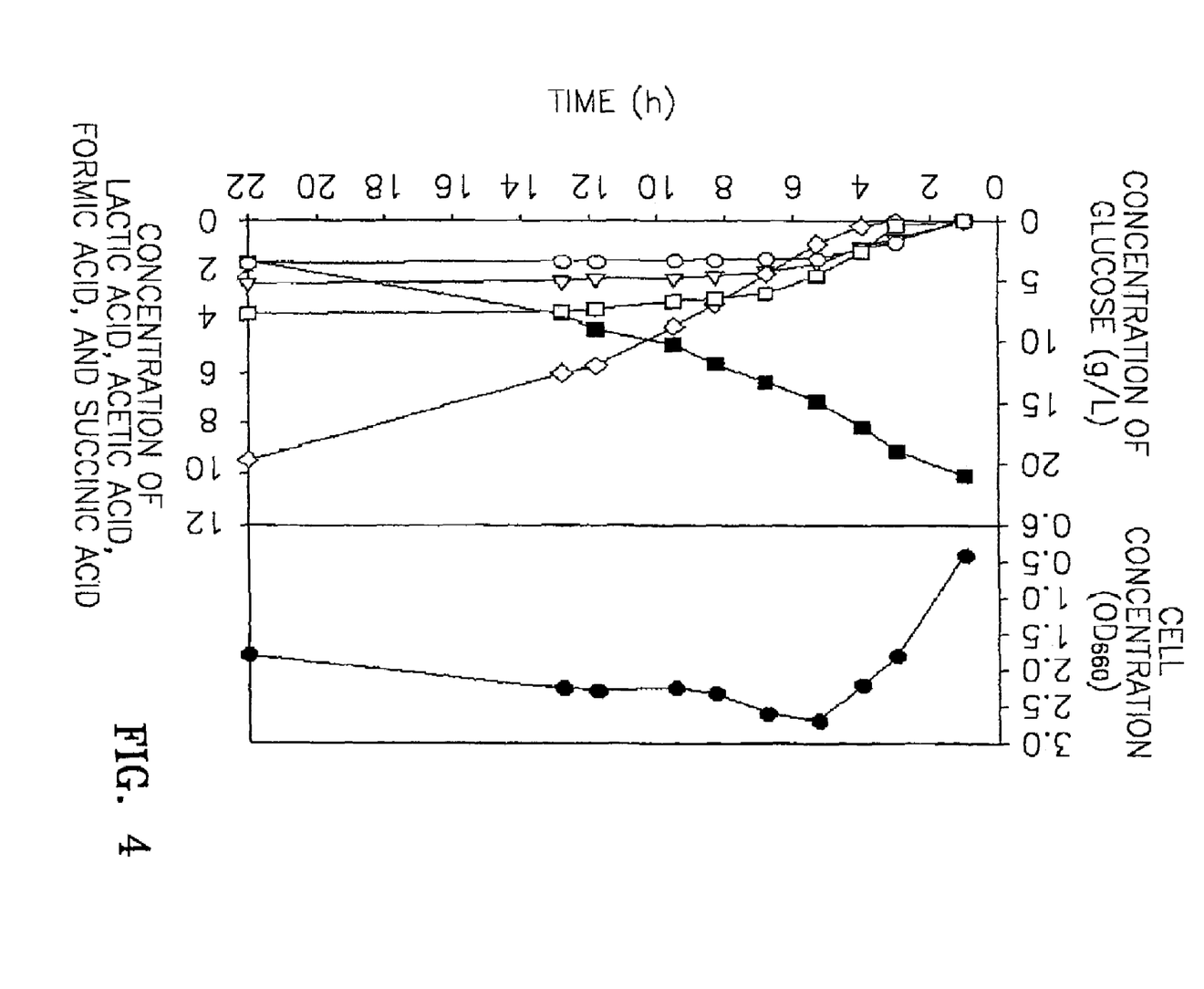
FIG. 4 is a graph showing the fermentation characteristics of *Mannheimia* sp. 55E under anaerobic conditions saturated with $N_2$.

FIG. 4 is a graph showing variations in concentration of cells (●), succinic acid (○), lactic acid (◇), glucose (■), formic acid (□), and acetic acid (Δ) with respect to incubation time. Unlike the result of FIG. 3, as shown in FIG. 4, *Mannheimia* sp. 55E according to the present invention produces lactic acid as a major product and succinic acid with a low yield less than 9% under anaerobic conditions saturated with $N_2$. During the anaerobic fermentation, 18 g/L of glucose is consumed, and 9.8 g/L lactic acid is produced with a yield of 54% and a volumetric productivity of 0.45 g/L/h.

This result indicates that *Mannheimia* sp. 55E needs $CO_2$ to produce succinic acid. *Mannheimia* sp. 55E is considered as fixing $CO_2$ to use it in the production of succinic acid.

EXAMPLE 5

Fermentation Characteristics of *Mannheimia* sp. 55E Under Aerobic Conditions Saturated with $O_2$ To investigate fermentation power of *Mannheimia* sp. 55E under aerobic conditions, incubation was carried out for 14 hours in the same manner as in Example 3, except that oxygen was supplied at a flow rate of 0.75 vvm. Culture media were sampled at 1-hour intervals during the incubation, and cell concentration and the amounts of lactic acid, glucose, and acetic acid were measured by the same method as in Example 3.

Figure 5:
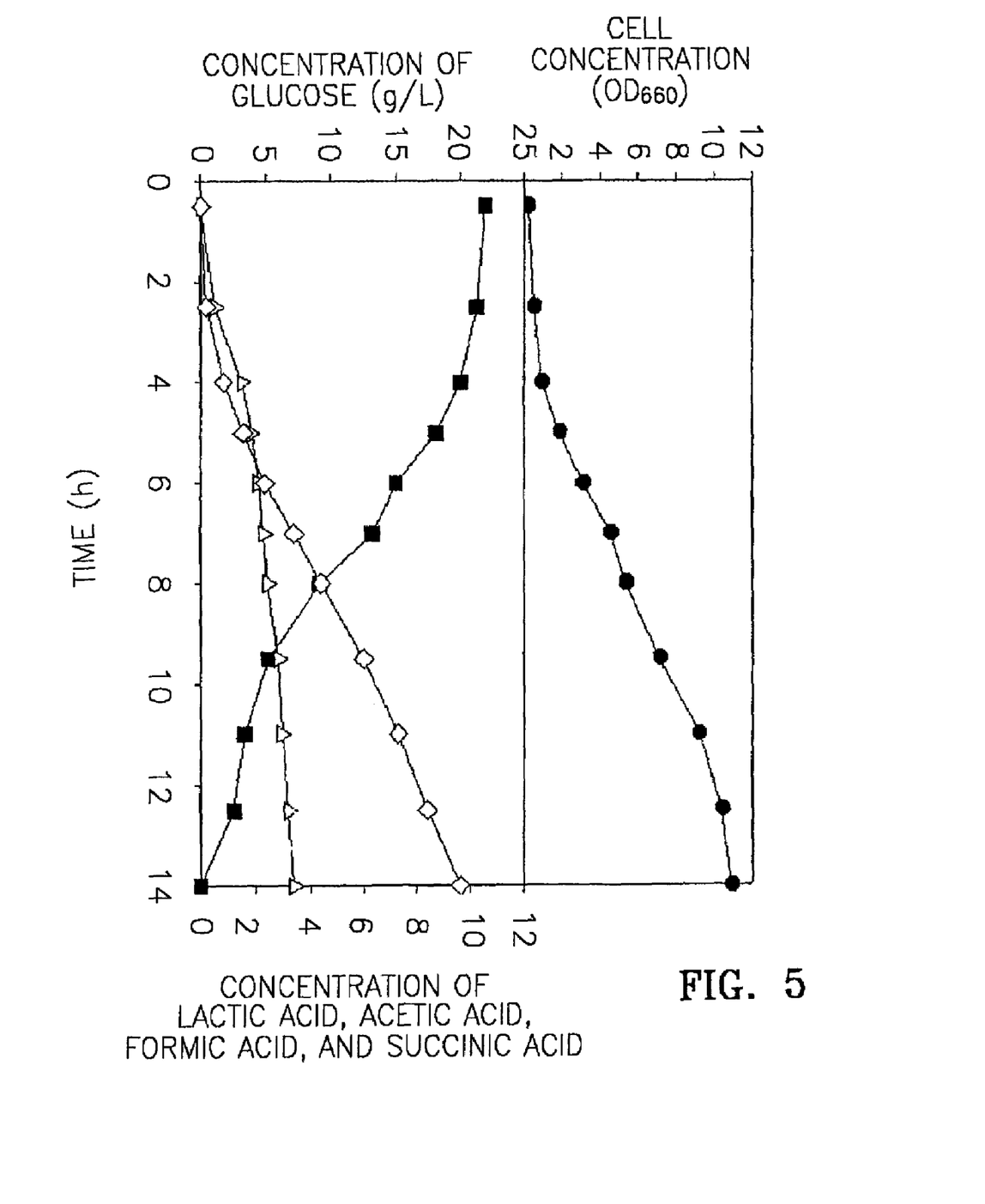
FIG. 5 is a graph showing the fermentation characteristics of *Mannheimia* sp. 55E under aerobic conditions.

FIG. 5 is a graph showing variations in concentration of cells (●), lactic acid (◇), glucose (■), and acetic acid (Δ) with respect to incubation time. As shown in FIG. 5, *Mannheimia* sp. 55E according to the present invention shows an increase in cell concentration up to 11 by optical density (OD) at 660 nm after fermentation under $O_2$ aerobic conditions. This result indicates that *Mannheimia* sp. 55E is a facultative anaerobe whose cell growth is unaffected by the presence of oxygen. This aerobic fermentation using *Mannheimia* sp. 55E does not produce succinic acid and formic acid at all and produces lactic acid as a major product. During the aerobic fermentation, 22 g/L of glucose is consumed, and 9.8 g/L lactic acid is produced with a yield of 45% and a volumetric productivity of 0.7 g/L/h.

As supported by the results described above, since *Mannheimia* sp. 55E according to the present invention is a facultative anaerobe, removal of dissolved oxygen is unnecessary for the production of succinic acid under $CO_2$ anaerobic conditions. It is expected that the production of succinic acid be unaffected by the presence of oxygen, as long as the amount of $CO_2$ supplied for the fermentation is sufficient enough.

The present invention provides *Mannheimia* sp. 55E, a novel microorganism capable of producing organic acids, and a process for producing organic acid through anaerobic and aerobic fermentation using the novel microorganism. As described above, *Mannheimia* sp. 55E according to the present invention produces succinic acid, lactic acid, and formic acid under $CO_2$ anaerobic conditions, and succinic acid, lactic acid, acetic acid, and formic acid under aerobic or $N_2$ anaerobic conditions. *Mannheimia* sp. 55E according to the present invention is a facultative anaerobe tolerant of oxygen. Thus, the use of *Mannheimia* sp. 55E in producing organic acids can eliminate a problem of process instability, which would occur by the presence of oxygen in the conventional fermentation process of producing organic acids using an obligate anaerobic microorganism.

While this invention has been particularly shown and described with reference to preferred embodiments thereof, it will be understood by those skilled in the art that various changes in form and details may be made therein without departing from the spirit and scope of the invention as defined by the appended claims.

---

---

What is claimed is:

1. *Mannheimia* sp. 55E with Accession Number KCTC 0769BP, capable of producing an organic acid under anaerobic and aerobic conditions.

2. A process for producing an organic acid, the process comprising:
    incubating *Mannheimia* sp. 55E with Accession Number KCTC 0769BP of claim 1 in a medium containing 5–60 g/L of glucose under anaerobic conditions saturated with carbon dioxide or nitrogen; and
    obtaining an organic acid from the medium.

3. The process of claim 2, wherein the organic acid is one of succinic acid, formic acid, acetic acid, and lactic acid.

4. The process of claim 2, wherein the incubation is carried out at a temperature of 35–45° C. at a pH of 6.0–7.5 with a supply of carbon dioxide or nitrogen at a flow rate of 0.1–0.4 vvm.

5. A process for producing succinic acid, the process comprising:

incubating *Mannheimia* sp. 55E with Accession Number KCTC 0769BP of claim 1 in a medium containing 5–60 g/L of glucose at a temperature of 35–45° C. at a pH of 6.0–7.5 with a supply of carbon dioxide at a flow rate of 0.1–0.4 vvm; and obtaining succinic acid from the medium.

6. A process for producing lactic acid, the process comprising:

incubating *Mannheimia* sp. 55E with Accession Number KCTC 0769BP of claim 1 in a medium containing 5–60 g/L of glucose at a temperature of 35–45° C. at a pH of 6.0–7.5 with a supply of nitrogen at a flow rate of 0.1–0.4 vvm; and obtaining lactic acid from the medium.

7. A process for producing an organic acid, the process comprising:

incubating *Mannheimia* sp. 55E with Accession Number KCTC 0769BP of claim 1 in a medium containing 5–60 g/L of glucose under aerobic conditions; and obtaining an organic acid from the medium.

8. The process of claim 7, wherein the organic acid is one of lactic acid and acetic acid.

9. The process of claim 7, wherein the incubation is carried out at a temperature of 35–45° C. at a pH of 6.0–7.5 with a supply of oxygen at a flow rate of 0.5–1.0 vvm.

10. A process for producing lactic acid, the process comprising:

incubating *Mannheimia* sp. 55E with Accession Number KCTC 0769BP of claim 1 in a medium containing 5–60 g/L of glucose at a temperature of 35–45° C. at a pH of 6.0–7.5 with a supply of oxygen at a flow rate of 0.5–1.0 vvm; and obtaining lactic acid from the medium.

* * * * *

UNITED STATES PATENT AND TRADEMARK OFFICE
CERTIFICATE OF CORRECTION

| | |
|---|---|
| PATENT NO. | : 7,063,968 B2 |
| APPLICATION NO. | : 10/312932 |
| DATED | : June 20, 2006 |
| INVENTOR(S) | : Lee et al. |

It is certified that error appears in the above-identified patent and that said Letters Patent is hereby corrected as shown below:

Title Page:
Item (73) Assignees, delete "Bisinformatix, Inc. (KR)"

Signed and Sealed this

First Day of May, 2007

JON W. DUDAS
*Director of the United States Patent and Trademark Office*

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
agagtttgat cmtggctcag                                            20

<210> SEQ ID NO 2
<211> LENGTH: 17
<212> TYPE: DNA
<213> ORGANISM: Artificial Sequence
<220> FEATURE:
<223> OTHER INFORMATION: primer

<400> SEQUENCE: 2
aaggaggtgw tccarcc                                               17
```